(12) United States Patent
Takii

(10) Patent No.: US 8,596,789 B2
(45) Date of Patent: Dec. 3, 2013

(54) NON-CONTACT TONOMETER

(75) Inventor: Michihiro Takii, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 1131 days.

(21) Appl. No.: 12/379,421

(22) Filed: Feb. 20, 2009

(65) Prior Publication Data

US 2009/0216106 A1   Aug. 27, 2009

(30) Foreign Application Priority Data

Feb. 27, 2008   (JP) ................................ 2008-045685

(51) Int. Cl.
*A61B 3/10*   (2006.01)
*A61B 3/00*   (2006.01)
*A61B 3/16*   (2006.01)

(52) U.S. Cl.
CPC ............... *A61B 3/0008* (2013.01); *A61B 3/165* (2013.01)
USPC ............................ 351/221; 351/214; 351/207

(58) Field of Classification Search
CPC .................................. A61B 3/103; A61B 3/107
USPC ......... 351/205, 207, 208, 210, 211, 212, 213, 351/214
See application file for complete search history.

(56) References Cited

U.S. PATENT DOCUMENTS

| | | | |
|---|---|---|---|
| 5,474,066 A | | 12/1995 | Grolman |
| 5,502,521 A | | 3/1996 | Katou |
| 5,946,073 A | * | 8/1999 | Miwa ............................. 351/205 |
| 6,120,444 A | * | 9/2000 | Miyakawa et al. ........... 600/401 |
| 7,695,139 B2 | * | 4/2010 | Ishikura ........................ 351/208 |
| 2006/0241367 A1 | | 10/2006 | Koest |
| 2007/0097317 A1 | | 5/2007 | Hayashi et al. |

FOREIGN PATENT DOCUMENTS

| | | |
|---|---|---|
| DE | 20 2005 002 562 U1 | 6/2005 |
| JP | A-63-197433 | 8/1988 |
| JP | A-07-023907 | 1/1995 |
| JP | A-07-059736 | 3/1995 |
| JP | A-07-222721 | 8/1995 |
| JP | A-08-507463 | 8/1996 |
| JP | A-2008-011878 | 1/2008 |
| JP | A-2008-11878 | 1/2008 |
| WO | WO 95/20342 A1 | 8/1995 |

* cited by examiner

*Primary Examiner* — Huy K Mai

(74) *Attorney, Agent, or Firm* — Oliff and Berridge, PLC

(57) ABSTRACT

A tonometer for measuring intraocular pressure of an examinee's eye in a non-contact manner, comprises: an arithmetic part for calculating the intraocular pressure; a fluid blowing unit for blowing a fluid at a cornea of the examinee's eye through a nozzle; a projecting optical system for projecting light onto an anterior segment of the examinee's eye through the nozzle, the system including a light source and a condensing lens; and an imaging optical system for imaging a cross-sectional image of the anterior segment, the system including an imaging lens and an imaging elements. The imaging optical system is placed so that extended planes of a cross section of the light projected onto the anterior segment by the projecting optical system, a principal plane of the imaging lens, and an imaging plane of the imaging element intersect one another on one axis, and the projecting optical system includes a light restriction unit that allows the light from the light source to pass through inside of the nozzle but not to pass through outside of the nozzle.

5 Claims, 3 Drawing Sheets

NON-CONTACT TONOMETER

TECHNICAL FIELD

The present invention relates to a tonometer for measuring intraocular pressure of an examinee's eye in a non-contact manner.

BACKGROUND ART

There is a tonometer for measuring intraocular pressure of an examinee's eye by blowing a fluid at a cornea of the examinee's eye through a nozzle and then optically detecting a deformed state of the cornea. As such tonometer, a device having an optical system for measuring corneal thickness by imaging (picking up) a cross-sectional image of an anterior segment of an examinee's eye including a cornea has been proposed. This device is arranged to correct measured intraocular pressure based on the measured corneal thickness (see WO 95/20342 (JP National publication No. 8(1996)-507463) and others).

SUMMARY OF INVENTION

Technical Problem

In the device (an optical system) of WO 95/20342, the imaged cross-sectional image is in focus on and near the center of a corneal anterior surface but is not in focus on a peripheral part of the corneal anterior surface and a corneal posterior surface. Thus, the corneal thickness could not be accurately measured and the intraocular pressure also could not be accurately corrected based on such corneal thickness.

The present invention has a purpose to provide a tonometer capable of accurately correcting intraocular pressure by accurately measuring corneal thickness.

Solution to Problem

To achieve the above object, the present invention provides tonometer for measuring intraocular pressure of an examinee's eye in a non-contact manner, the tonometer comprising: an arithmetic part for calculating the intraocular pressure; a fluid blowing unit for blowing a fluid at a cornea of the examinee's eye through a nozzle; a projecting optical system for projecting light onto an anterior segment of the examinee's eye through the nozzle, the system including a light source and a condensing lens; and an imaging optical system for imaging a cross-sectional image of the anterior segment, the system including an imaging lens and an imaging element; wherein the imaging optical system is placed so that extended planes of a cross section of the light projected onto the anterior segment by the projecting optical system, a principal plane of the imaging lens, and an imaging plane of the imaging element intersect one another on one axis, and the projecting optical system includes a light restriction unit that allows the light from the light source to pass through inside of the nozzle but not to pass through outside of the nozzle.

DESCRIPTION OF EMBODIMENTS

Figure 1:
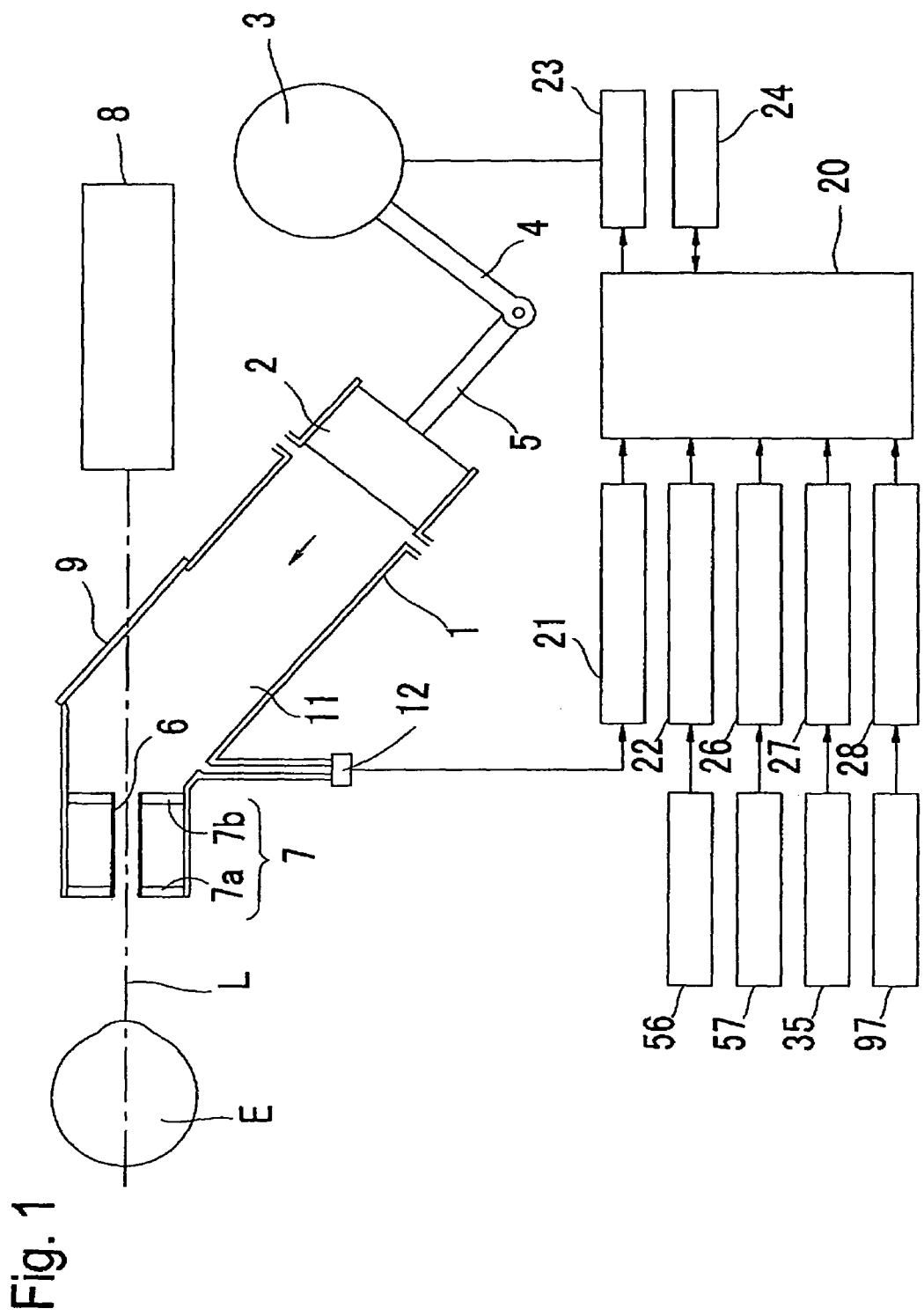
FIG. 1 is a schematic configuration view of a fluid blowing mechanism of a non-contact tonometer of a preferred embodiment of the present invention.
Figure 2:
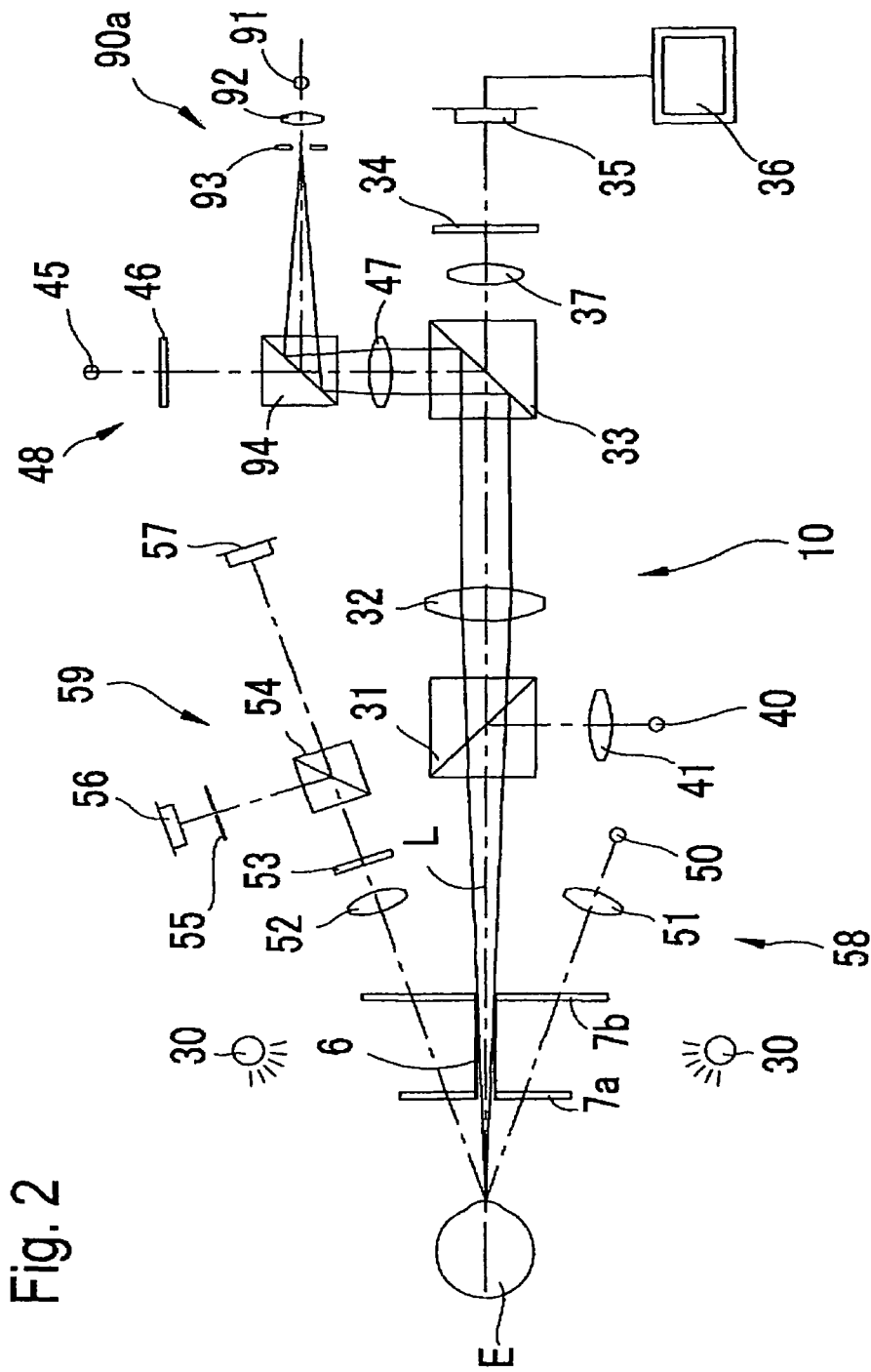
FIG. 2 is a schematic configuration view of optical systems of the tonometer.

A detailed description of a preferred embodiment of the present invention will now be given referring to the accompanying drawings. FIG. 1 is a schematic configuration view (partly including a block diagram of a control system) of a fluid blowing mechanism of a non-contact tonometer in this embodiment. FIG. 2 is a schematic configuration view of optical systems of the tonometer.

An air compression cylinder 1 is arranged at a slant with respect to a horizontal line of a main body of a device (a tonometer). When a rotary solenoid 3 is supplied with driving energy, a piston 2 is moved upward within the cylinder 1 through an arm 4 and a piston rod 5. Air in an air compression chamber 11 communicating with the cylinder 1 is compressed by upward movement of the piston 2 and is emitted at a cornea of an examinee's eye E through a nozzle 6. The solenoid 3 is provided with a coil spring not shown. When the supply of the driving energy is stopped, the piston 2 having been moved upward is moved downward by an urging force of the coil spring that urges the piston 2 in a downward direction.

Transparent glass plates 7 (7a and 7b) serve as a holding member for holding the nozzle 6 and also a transmitting member that transmits light as mentioned later. One glass plate 7a placed on a side near the eye E is a protecting member for preventing foreign substances from entering from outside into inside. The other glass plate 7b is a member constituting a part of the air compression chamber 11. A transparent glass plate 9 is placed at the rear of the nozzle 6 and is a member constituting a part of the air compression chamber 11 and also a transmitting member that transmits light as mentioned later. At the rear of the glass plate 9, an anterior-segment observation and alignment optical system 8 is arranged.

Connected to an arithmetic control circuit 20 such as a CPU are a pressure detection processing circuit 21 for a pressure sensor 12 for detecting pressure in the air compression chamber 11, a signal detection processing circuit 22 for a light detector 56 mentioned later, a signal detection processing circuit 26 for a one-dimensional position detecting element 57 mentioned later, a signal detection processing circuit 27 for a two-dimensional imaging element 35 mentioned later, a signal detection processing circuit 28 for a two-dimensional imaging element 97 mentioned later, a drive circuit 23 for the rotary solenoid 3, a memory 24 for storing measurement data and others, light sources mentioned later, a monitor 36, and others.

A front image of the anterior segment of the eye E illuminated by an infrared light source 30 for observation of an anterior segment passes through a beam splitter (a half mirror) 31, an objective lens 32, a beam splitter (a dichroic mirror) 33, an imaging lens 37, and a filter 34, and is formed on the imaging element 35 such as a CCD camera. The beam splitter 33 has a property of transmitting infrared light (light from the light source 30, light from a light source 40 mentioned later, and light from a light source 50 mentioned later) and reflecting visible light (light from a light source 45 mentioned later and light from a light source 91 mentioned later). The filter 34 has a property of transmitting the light from the light source 30 and the light from the light source 40 mentioned later and blocking the light from the light source 50 mentioned later and the visible light. An image formed on the imaging element 35 is displayed on the monitor 36.

The light from the infrared light source 40 for alignment passes through a projection lens 41 and is reflected by the beam splitter 31, and the light is projected onto the eye E from the center front. A corneal luminescent spot (a corneal reflection image) formed at the vertex of the cornea by the light from the light source 40 passes through the beam splitter 31 to the filter 34 and then forms an image on the imaging element 35. The arithmetic control circuit 20 obtains alignment information of the device (the optical system) in vertical and lateral directions relative to the eye E based on an output signal from the imaging element 35.

The light from the visible light source 45 for projecting a fixation target illuminates a fixation target 46 passes through a beam splitter (a dichroic mirror) 94 and a projection lens 47 and is reflected by the beam splitter 33. The reflected light passes through the lens 32 and the beam splitter 31 and then is projected onto the eye E from the center front. The beam splitter 94 has a property of transmitting the light from the light source 45 and reflecting the light from the light source 91 mentioned later. The above components constitute a fixation target projecting optical system 48.

The light from the infrared light source 50 for detecting a corneal deformed state is converted into a substantially parallel light flux by a collimator lens 51 and is projected onto the eye E obliquely from the front. The light from the light source 50, reflected by the cornea, passes through a right-receiving lens 52 and a filter 53 and is reflected by a beam splitter (a half mirror) 54. The reflected light passes through a pin hole 55 and then is received by the light detector 56. The filer 53 has a property of transmitting the light from the light source 50 and blocking the light from the light source 30, the light from the light source 40, and the visible light. A corneal deformed state detecting optical system constituted by the above components is disposed so that an amount of the light received by the light detector 56 is maximum when the cornea is in a predetermined deformed state (a flattened state).

The light from the light source 50, reflected by the cornea, passes through the lens 52, the filter 53, and the beam splitter 54 and enters the positional detecting element 57 such as a PSD and a line sensor. As the eye E moves forward or backward (in a working distance direction), an incident position of the light from the light source 50 also moves on the position detecting element 57. Accordingly, the arithmetic control circuit 20 obtains the alignment information of the device in forward and backward directions relative to the eye E based on an output signal from the position detecting element 57. A working distance detecting optical system constituted by the above components is disposed so that the light from the light source 50 enters the center of the position detecting element 57 when the cornea is located at a predetermined working distance.

Figure 3:
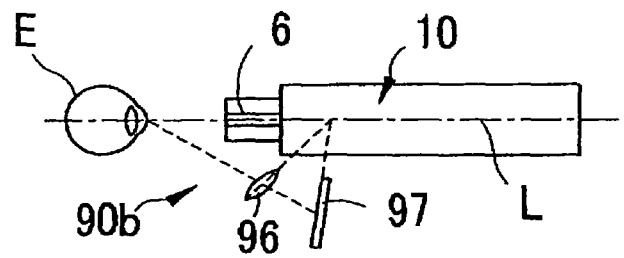
FIG. 3 is a schematic optical view of an imaging optical system for measuring corneal thickness.

In this embodiment, a corneal thickness measuring optical system is provided to image a cross-sectional image of the anterior segment of the eye E to thereby measure corneal thickness of the eye E. This optical system includes a projecting optical system 90a for projecting the light for imaging the anterior-segment cross-sectional image onto the anterior segment through the nozzle 6 and an imaging optical system 90b (see FIG. 3) for receiving the reflection light from the anterior segment to image the anterior-segment cross-sectional image. The projecting optical system 90a includes the visible light source 91 for imaging a anterior-segment cross-sectional image, a condensing lens 92, a slit 93 oriented so that its longitudinal side is horizontal, the beam splitter 94, the lens 47, the beam splitter 33, and the lens 32 to project slit light onto the eye E. The slit 93 is placed in a position conjugated with the anterior segment (e.g., near the corneal apex). The slit 93 may be selected from a glass plate, a metal plate, or others if only it is formed with a slit and applied with a coating around the slit to block the light from the light source 91. The light source 91 used herein is for example a light source that emits light (blue light) in a wavelength region of 460 nm to 490 nm having a center wavelength of 470 nm. Furthermore, the lenses 47 and 32 are arranged between the light source 91 and the nozzle 6 and used as a light condensing optical system (a condensing lens) for condensing the light from the light source 91 to the anterior segment.

The projecting optical system 90a includes a light restriction member that allows the light from the light source 91 to pass through the inside of the nozzle 6 and not to pass through the outside of the nozzle 6 Specifically, the glass plate 7a and/or the glass plate 7b holding the nozzle 6 are/is used as a filter for blocking a wavelength region of the light from the light source 91 This filter is applied with a coating or the like to have, for example, a property of transmitting the light for anterior-segment observation (the light from the light source 30) and the light for alignment (the light from the light source 40 and the light from the light source 50) and blocking the light for imaging an anterior-segment cross-sectional image (the light from the light source 91). In this embodiment, the glass plate 7a is used as the filter.

The imaging optical system 90b includes an imaging lens 96 whereby the reflection light from the anterior segment by the projecting optical system 90a is introduced to the imaging element 97, and the imaging element 97 such as a CCD camera. This imaging optical system 90b is arranged to image an anterior segment cross-sectional image by imaging, based on the Scheimpflug principle, a cross-sectional image by the slit light projected onto the anterior segment. Specifically, the imaging optical system 90b has an optical arrangement so that extended planes of a cross section of the slit light projected onto the anterior segment by the projecting optical system 90a, a principal plane of the imaging lens 96, and an imaging plane of the imaging element 97 intersect one another on one intersection line (one axis). It is to be noted that the imaging optical system 90b is disposed blow the aforementioned intraocular pressure measuring optical system 10 so as to avoid the slit light from becoming eclipsed by the examinee's nose.

The light from the light source 91 is condensed by the lens 92 and illuminates the slit 93. The light having passed through the slit 93 forms the slit light. The slit light is made coaxial with the light of the fixation target by the beam splitter 94, then converted into a substantial parallel light flux by the lens 47, and is reflected by the beam splitter 33 and converged by the lens 32. Only the light having passed through the inside of the nozzle 6 is condensed on the anterior segment. Thus, the slit light having passed through the inside of the nozzle 6 forms a slit cross-sectional image on the anterior segment.

Figure 4:
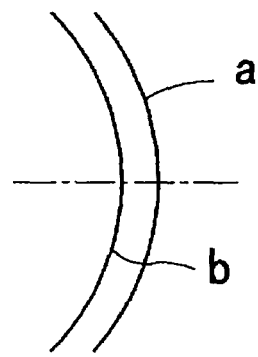
FIG. 4 is a view showing a corneal cross-sectional image which is a part of an anterior-segment cross-sectional image imaged by an imaging device of the imaging optical system for measuring corneal thickness.

The slit cross-sectional image formed on the anterior segment as mentioned above is imaged by the imaging element 97 through the imaging lens 96. FIG. 4 shows a corneal cross-sectional image which is a part of the anterior-segment cross-sectional image imaged by the imaging element 97. In FIG. 4, "a" indicates a corneal anterior surface and "b" indicates a corneal posterior surface. Herein, the arithmetic control circuit 20 calculates the corneal thickness of the eye E by image processing (for details, refer to JP 63(1988)-197433).

In this case, the corneal thickness may be calculated from the entire cross-sectional image (for example, by averaging values measured at different points) or may be determined at a certain point (for example, a position passing through the corneal center). The arithmetic control circuit 20 calculates a corneal curvature based on the corneal cross-sectional image and corrects the corneal thickness.

The operation of the device configured as above will be described below. An examiner asks an examinee to place the eye E in a predetermined position and performs alignment of the device relative to the eye E by operating a joystick not illustrated. For details of this alignment, refer to U.S. Pat. No. 5,502,521 (JP7(1995)-23907) and others.

When detecting completion of alignment based on the alignment information obtained from the imaging element 35 and the positional detecting element 57, the arithmetic control circuit 20 automatically generates a trigger signal for measurement start (or receives input of a trigger signal by the examiner) to start measurement.

Upon generation of the trigger signal, the arithmetic control circuit 20 causes the light source 91 to emit light and the imaging element 97 to image the anterior-segment cross-sectional image, and supplies driving energy to the solenoid 3 before completion of imaging of the cross-sectional image so as to drive the solenoid 3 to blow a fluid at the cornea after the imaging of the cross-sectional image is completed.

Figure 5:
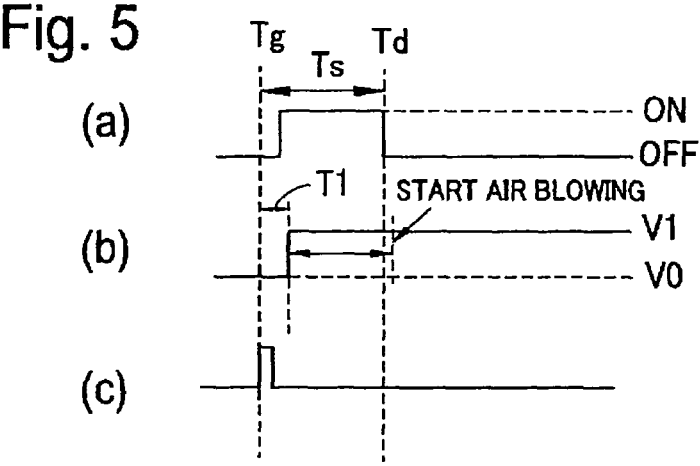
FIG. 5 is a view showing a concrete example of timings for imaging the anterior-segment cross-sectional image and measuring the intraocular pressure based on a trigger signal.

FIG. 5 is a concrete example of timings at which the anterior-segment cross-sectional image is obtained and intraocular pressure is measured based on the trigger signal. In FIG. 5, specifically, (a) shows a timing for turning on the light source 91 or increasing an amount of light having been previously emitted from the light source 91 and a timing for turning off the light source 91 or returning the light emission amount to an original emission amount, (b) shows a timing for supplying the driving energy to the solenoid 3, and (c) shows a timing at which the trigger signal is generated. Herein, the arithmetic control circuit 20 turns on the light source 91 to emit light for a predetermined time according to the trigger signal to obtain the cross-sectional image by the imaging element 97, and stores the cross-sectional image in the memory 24. Herein, when the light emission time of the light source 91 is 1/60 second, the imaging element 97 completes acquisition of the cross-sectional image for 1/60 second.

The arithmetic control circuit 20 supplies the driving energy to the solenoid 3 at a stage prior to completion of imaging of the cross-sectional image by the imaging element 97 (see "Td" in (a) to (c) in FIG. 5). In this case, for example, a time (duration) Ts from turn-on (light emission start) of the light source 91 in response to the trigger signal to turn-off of the light source 91 and a time from start of supply of the driving energy to the solenoid 3 to arrival of air at the cornea (for example, about 1/60 second) are found in advance by experiments or the like. Further, a time T1 from a trigger time Tg at which the trigger signal is generated to the start of the supply of the driving energy to the solenoid 3 is calculated in advance so that the driving energy is supplied to the solenoid 3 after generation of the trigger signal and during or before light emission of the light source 91 to start blowing of air at the cornea after turn-off of the light source 91 (after completion of acquisition of the cross-sectional image). This may be set as a timing for supplying the driving energy to the solenoid 3. Thus, the air can be quickly blown at the cornea after acquisition of the cross-sectional image. The measurement of intraocular pressure can be completed before a fixation state of the eye E becomes unstable due to glare resulting from the light emission of the light source 91 or an increase in the emission light amount. The measurement can therefore be conducted smoothly.

When the solenoid 3 is supplied with the driving energy, the air is blown at the cornea from the nozzle 6. Thus, the cornea is gradually deformed by the blown air. The light from the light source 50, reflected by the cornea, enters the light detector 56, so that a deformed state of the cornea is detected based on an output signal from the light detector 56.

The cornea is gradually deformed by air blowing into a flattened state at which a maximum light amount enters the light detector 56. The arithmetic control circuit 20 calculates the intraocular pressure based on an output signal from the pressure sensor 12 when the cornea is deformed into the flattened state.

Subsequently, the arithmetic control circuit 20 calculates the corneal thickness of the eye E based on the imaged anterior-segment cross-sectional image and corrects the calculated intraocular pressure of the eye E based on the calculated corneal thickness (for example, see WO 95/20342). The measured value of the corneal thickness and the corrected measured value of the intraocular pressure are displayed on the monitor 36.

With the above configuration, the slit cross-sectional image can be prevented from blurring due to a difference in optical path length between the light passing through the inside of the nozzle 6 and the light passing through the glass plates 7 placed outside the nozzle 6 (the light passing through the glass plates 7 has a longer optical path length). Accordingly, the slit light from the light source 91 can create a clear anterior-segment cross-sectional image with less blur. It is therefore possible to appropriately correct the intraocular pressure based on the corneal thickness.

The above-mentioned configuration is arranged to project the slit light onto the cornea. An alternative is to project a spot light onto the cornea and image a corneal cross-sectional view by a spot image projected on the cornea, thereby calculating the corneal thickness. For instance, the slit 93 placed in a conjugated relation with the cornea is replaced with a circular hole and a corneal cross-sectional image is imaged by the imaging optical system 50b. In this case, it is conceivable to use a circular hole having a diameter nearly equal to the width of a short side of the slit 93. This makes it possible to obtain a cross-sectional image at and near the corneal center and thus the corneal thickness at and near the corneal center can be measured.

In the above-mentioned configuration, the imaging optical system 90b is placed below the intraocular pressure measuring optical system 10. An alternative is to place the imaging optical system 90b on the left or right of the measuring optical system 10. In this case, the imaging optical system 90b needs to be placed in a position where the slit light is not eclipsed by the nozzle 6.

In the above explanation, in order to allow the light traveling toward the anterior segment from the light source 91 to pass through the inside of the nozzle 6 but not to pass through the outside of the nozzle 6, the glass plates 7 blocks the light. However, any other configuration may also be adopted. For instance, an aperture diaphragm formed to allow the light traveling toward the anterior segment from the light source 91 to pass through the inside of the nozzle 6 but not to pass through the outside of the nozzle 6 may be provided in the optical path between the light source 91 and the nozzle 6 (e.g., between the slit plate 93 and the projection lens 47).

In the case of using a target projecting optical system 58 (the light source 50 and the lens 51) for projecting an alignment target onto the cornea obliquely from the front through the glass plates 7 and a target detecting optical system 59 (from the lens 52 to the position detecting element 57) having an optical axis nearly symmetric with an optical axis of the target projecting optical system 58 relative to an axis line L of the nozzle 6 coaxial with an optical axis of the measuring optical system 10 (the lens 32 and others), the optical system 59 being arranged to detect the alignment target projected onto the cornea and reflected through the glass plates 7, it is preferable to form an antireflection film on the glass plates 7 in order to prevent back reflection of the light from the light source 91. This can prevent the light from the light source 91 from entering the position detecting element 57, thereby avoiding difficulty in detecting the alignment state.

In the above explanation, the transparent flat glass plates 7 are used as the optical member holding the nozzle 6 and having a property of transmitting at least the light from the light source 30 (the reflection light from the anterior segment) but the invention is not limited thereto. For instance, it may be configured that a nozzle is formed through the center of an objective lens and this objective lens is used as an objective lens of the optical system (e.g., the anterior segment observation optical system) placed in a housing of the device. In this case, the objective lens has only to be applied with a coating or the like to allow the light from the light source for corneal thickness measurement to pass through the inside of the nozzle but not to pass through the outside of the nozzle.

In the above explanation, the light source 91 of the projecting optical system 90a for corneal thickness measurement and the light source 45 of the fixation target projecting optical system 48 are separately provided but a single light source may be used in common between the systems 90a and 48.

The invention claimed is:

1. A tonometer for measuring intraocular pressure of an examinee's eye in a non-contact manner, the tonometer comprising:
   an arithmetic part for calculating the intraocular pressure;
   a fluid blowing unit for blowing a fluid at a cornea of the examinee's eye through a nozzle;
   a projecting optical system for projecting light onto an anterior segment of the examinee's eye through the nozzle, the system including a visible light source that projects the light, a condensing optical system for condensing the light from the visible light source to the anterior segment, and an aperture placed in a position conjugated with the anterior segment; and
   an imaging optical system for imaging a cross-sectional image of the anterior segment, the system including an imaging lens and a first imaging element;
   an infrared light source for observing a front image of the examinee's eye;
   an optical member that holds the nozzle and transmits at least light from the infrared light source; and
   a second imaging element placed at a rear of the optical member and configured to form thereon a front image of the anterior segment illustrated by the infrared light source, wherein
   the imaging optical system is placed so that extended planes of a cross section of the light projected onto the anterior segment by the projecting optical system, a principal plane of the imaging lens, and an imaging plane of the imaging element intersect one another on one axis,
   the projecting optical system includes a light restriction unit that is placed off the position conjugated with the anterior segment and allows the light from the visible light source to pass through inside of the nozzle but not to pass through outside of the nozzle, and
   the light restriction unit is a filter placed around the nozzle that transmits the light from the infrared light source and blocks the light from the visible light source, or the light restriction unit is a diaphragm placed between the aperture and the nozzle that allows the light from the visible light source to pass through inside of the nozzle but does not allow the light from the visible light source to pass through outside of the nozzle.

2. The tonometer according to claim 1, further comprising:
   a transparent plate formed outside the nozzle;
   a target projecting optical system for projecting an alignment target obliquely from front onto the cornea through the transparent plate; and
   a target detecting optical system which has an optical axis nearly symmetric with an optical axis of the target projecting optical system with respect to an axis line of the nozzle and which detects the alignment target projected onto the cornea through the transparent plate;
   wherein the glass plate is formed with an antireflection film to prevent back reflection of the light emitted from the visible light source.

3. The tonometer according to claim 1, further comprising a trigger signal generating device which generates a trigger signal,
   wherein
   the fluid blowing unit is a fluid blowing mechanism having a drive part to blow the fluid at the cornea,
   the visible light source is caused to emit the light in response to the trigger signal and the anterior-segment cross-sectional image is imaged by the imaging element, and
   the drive part is supplied with driving energy before completion of imaging of the anterior-segment cross-sectional image to blow the fluid at the cornea after the completion of the imaging of the anterior-segment cross-sectional image.

4. The tonometer according to claim 1, wherein the arithmetic part calculates corneal thickness of the examinee's eye based on the imaged anterior-segment cross-sectional image and corrects the calculated intraocular pressure based on the calculated corneal thickness.

5. The tonometer according to claim 1, wherein the aperture includes one of a slit and a circular hole.

* * * * *